United States Patent [19]

Sharma et al.

[11] Patent Number: 4,710,214
[45] Date of Patent: Dec. 1, 1987

[54] PROCESS FOR SEPARATION OF HYDROCARBON GASES

[75] Inventors: Shanmuk Sharma, Houston; Donnie K. Hill, Woodlands; Charles A. Durr, Houston, all of Tex.

[73] Assignee: The M. W. Kellogg Company, Houston, Tex.

[21] Appl. No.: 944,272

[22] Filed: Dec. 19, 1986

[51] Int. Cl.[4] ............................................. F25J 3/02
[52] U.S. Cl. .................................... 62/28; 62/34; 62/39; 62/44
[58] Field of Search ............... 62/23, 24, 27, 28, 32, 62/34, 36, 38, 39, 42, 44

[56] References Cited

U.S. PATENT DOCUMENTS

| | | | |
|---|---|---|---|
| 2,952,983 | 9/1960 | Gilmore | 62/27 X |
| 3,282,060 | 11/1966 | Hays | 62/24 |
| 3,292,380 | 12/1966 | Bucklin | 62/20 |
| 3,319,429 | 5/1967 | Pryor | 62/39 X |
| 3,675,435 | 7/1972 | Jackson et al. | 62/28 X |
| 4,203,742 | 5/1980 | Agnihotri | 62/24 |
| 4,272,270 | 6/1981 | Higgins | 62/24 |
| 4,331,461 | 5/1982 | Karbosky et al. | 62/28 |
| 4,444,577 | 4/1984 | Perez | 62/39 X |
| 4,486,209 | 12/1984 | Fabbri et al. | 62/34 X |
| 4,507,133 | 3/1985 | Khan et al. | 62/29 |

Primary Examiner—Albert J. Makay
Assistant Examiner—Steven E. Warner

[57] ABSTRACT

A process for separation of a high pressure gas stream such as light refinery gases in which the gas mixture is expanded, preferably through a turbine, and separated into first vapor and liquid portions. The first vapor portion may be recovered as, for example, methane-rich product gas. The first liquid portion is raised to an intermediate pressure, revaporized, and introduced to a fractionator from which an ethane-containing stream is recovered. The ethane-containing stream is then cooled and separated into a second vapor portion and a second liquid portion which is then expanded and combined with the expanded starting gas mixture to increase the amount of refrigeration that may be recovered from the first liquid stream prior to its fractionation.

4 Claims, 2 Drawing Figures

PROCESS FOR SEPARATION OF HYDROCARBON GASES

This invention relates to a process for cryogenic separation of high pressure, normally gaseous hydrocarbons. More particularly, the invention relates to a method for forming a cold process stream from which refrigeration may be recovered in greater amount than is possible by conventional, series expansions of cold recovery of the starting gas fractions. The process of the invention finds application in, for example, refinery gas separations, natural gas liquefaction, and natural gas liquids separation. The high pressure gas may also contain from 10 to 90 volume percent carbon dioxide or nitrogen resulting from well injection of these gases for enhanced oil recovery operations. The process is particularly well suited for use in the separation of $C_3$–$C_4$ hydrocarbons for sale as liquefied petroleum gas (LPG).

According to the invention, the high pressure gas stream is expanded to a first intermediate pressure and introduced to a first single equilibrium separation zone. A first liquid is separately recovered from the first separation zone, elevated in pressure to a second intermediate pressure, revaporized by recovery of refrigeration, and then introduced to a multi-equilibrium separation zone. An ethane-containing gaseous mixture is recovered from the multi-equilibrium separation zone, cooled, and introduced to a second single equilibrium separation zone from which a second vapor stream and a second liquid stream are separately recovered. The second liquid stream is then expanded into the first single equilibrium separation zone in mixture with the initially expanded gas.

Figure 1:
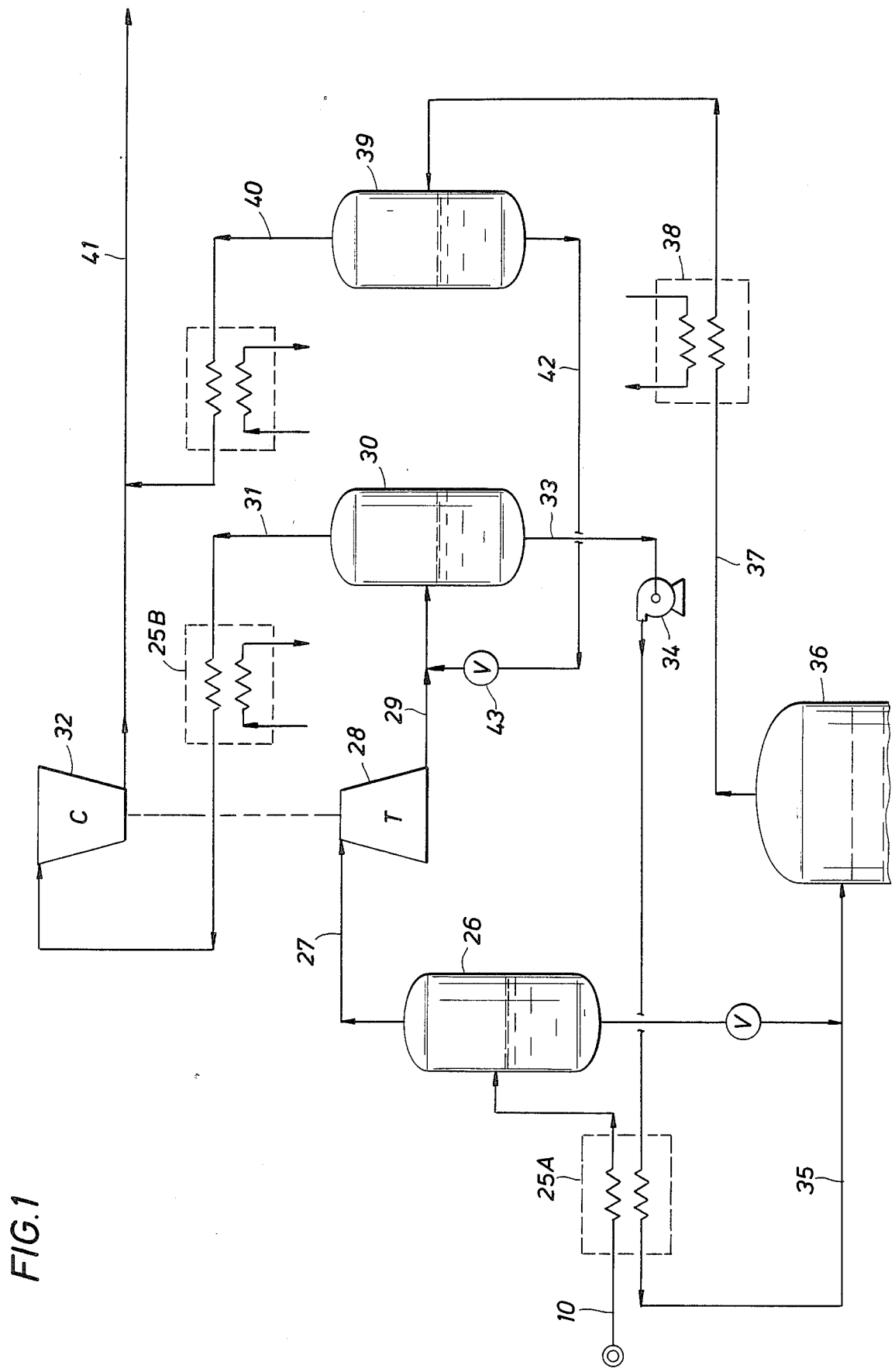
FIG. 1 is a flow diagram of the process of the invention.

Referring to FIG. 1, light gas containing, in for example refinery gas, principally methane, $C_2$ hydrocarbons, and hydrogen with lesser amounts of nitrogen and $C_3$ hydrocarbons is introduced to the separation system through line 10, cooled in exchanger 25, and separated in turbine feed flash drum 26. The vapor stream 27 from flash drum 26 is a high pressure gaseous stream containing mixed light hydrocarbons of similar composition to the starting light gas but with reduced $C_2$–$C_3$ hydrocarbon content. When the light gas is derived from natural gas obtained by enhanced oil recovery techniques employing injected nitrogen or carbon dioxide, the principal constituent of the high pressure gaseous stream in line 27 may be respectively nitrogen or carbon dioxide according to the depletion condition of the well. To great extent, nitrogen when present will follow the flow path of methane whereas carbon dioxide will follow the flow path of ethane. If such binary mixtures are not desired as products, they may be separated in specifically designed, downstream fractionation systems.

The gaseous feed to the process of the invention will preferably be at sufficiently high pressure to provide at least one stage of expansion from which refrigeration can be derived while still yielding a product gas from a fraction of the expanded gas at a useful delivery pressure typically in the range between 3 and 28 kg/cm$^2$a. The high pressure will typically be within the range from 5 to 55 kg/cm$^2$a.

High pressure gas stream 27, preferably pre-cooled in exchanger 25A with refrigeration developed in the process of the invention is expanded across turbine 28 to a first intermediate pressure typically between 3 and 35 kg/cm$^2$a and introduced through line 29 to flash drum 30 which is the first separation zone of the process of the invention. In this embodiment, shaft work from the turbine is employed to recompress a first vapor stream 31 from flash drum 30 in compressor 32 to product gas delivery pressure following recovery of refrigeration from the vapor stream in exchanger 25B.

A first liquid stream 33 is recovered from flash drum 30 separate from the vapor stream and elevated to a second intermediate pressure by pump 34. The second intermediate pressure will also typically be between 3 and 35 kg/cm$^2$a but will be above the first intermediate pressure. Refrigeration is then recovered from the first liquid stream in exchanger 25A and the resulting partially revaporized stream is introduced through line 35 to an upper feed point of de-ethanizer column 36 which is a multi-equilibrium separation zone. When the first liquid stream in line 35 is combined with let-down liquid from flash drum 26, the de-ethanizer column feed is principally $C_2$ and $C_3$ hydrocarbons, however, the $C_2$ component is only a minor portion of $C_2$ content of the starting light gas in line 10. In treatment of refinery gas, column 36 also receives somewhat heavier streams (not shown in FIG. 1) from other gas separation steps. Overhead stream 37 from column 36 contains principally ethane and ethylene with only small amounts of methane and $C_3$ hydrocarbons. When the process is used with nitrogen enhanced oil recovery this stream, as well as the first vapor stream, will be predominantly nitrogen. The overhead stream leaving the column is cooled to $-54°$ C. in exchanger 38 and then flashed into a second separation zone indicated by flash drum 39. Refrigeration is recovered from a second vapor stream 40 leaving this flash drum and the second vapor stream combined with the first vapor stream discharged from compressor 32 to form, in the case of refinery gas, a methane-rich product gas in line 41.

Since the column overhead stream 37 is at substantially the second intermediate pressure which, in this embodiment is 1.5 kg/cm$^2$ higher than the first intermediate pressure, the function of the second separation zone is to provide second liquid stream 42 which is expanded across valve 43 and combined with the turbine expanded stream in line 29. The mixture of these cold streams increases the amount of refrigeration beyond that obtainable by turbine expansion alone and thereby increases the refrigeration recovered in exchanger 25A.

The first and second separation zones indicated as flash drums 30 and 39 are single equilibrium separation zones which are well adapted for flashing $C_2$ and lighter gases for their respective feeds. Typical operating conditions for the separation zones are:

|  | Refinery Gas | Gas Liquids from Enhanced Oil Recovery with $N_2$ |
|---|---|---|
| First Separation Zone |  |  |
| Temperature (°C.) | −90 | −85 |
| Pressure (kg/cm$^2$a) | 4 | 28 |
| Second Separation Zone |  |  |
| Temperature (°C.) | −55 | −50 |
| Pressure (kg/cm$^2$a) | 5 | 35 |
| Turbine Feed Flash |  |  |

|  | Refinery Gas | Gas Liquids from Enhanced Oil Recovery with $N_2$ |
|---|---|---|
| Drum (26) | | |
| Temperature (°C.) | −65 | −60 |
| Pressure (kg/cm²a) | 12 | 55 |

Figure 2:
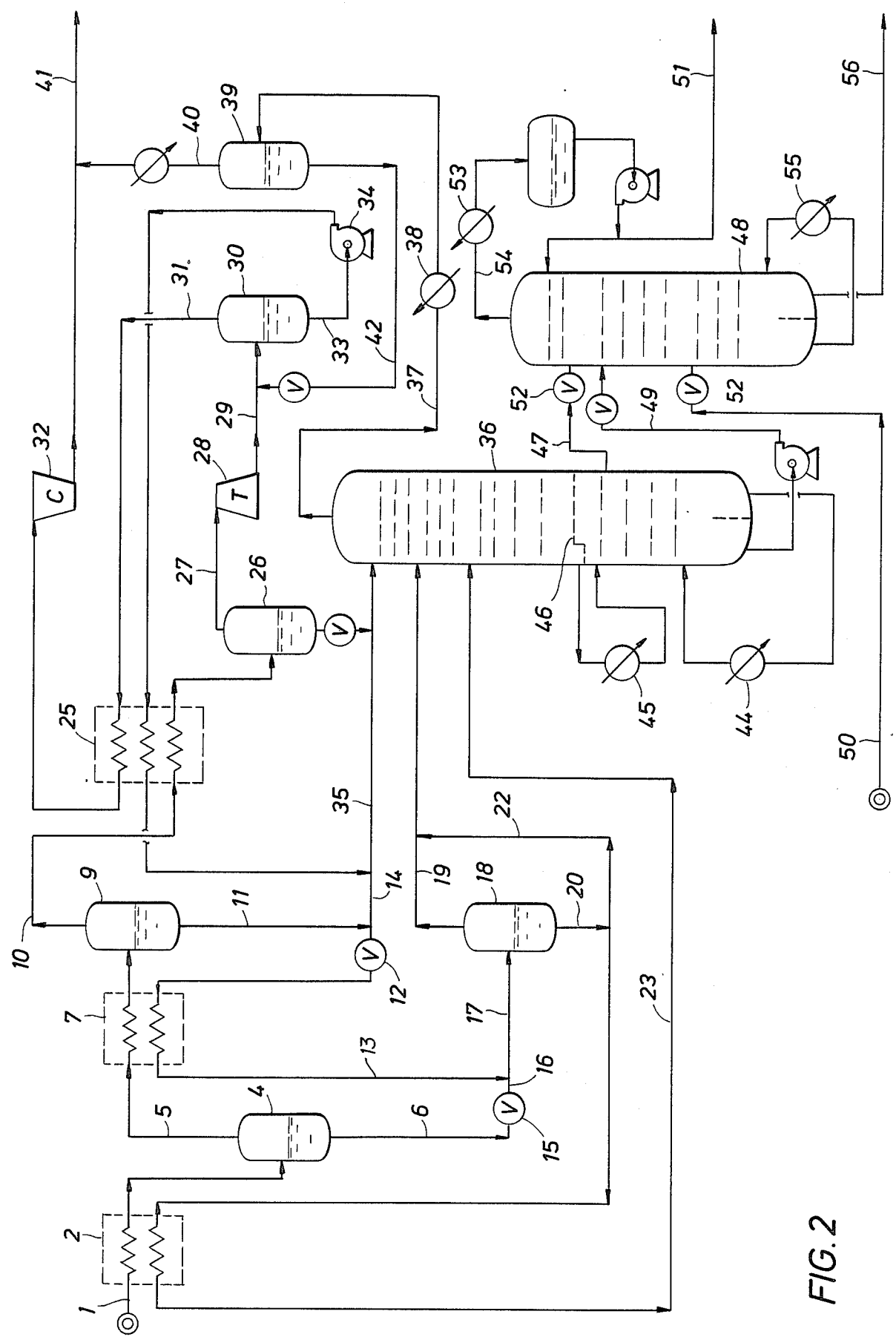
FIG. 2 is an overall flow diagram of a process for separation of refinery gases with the principal object of LPG production and illustrates use of the invention in the light gases section of a refinery gas flow scheme.

Referring now to FIG. 2 in which reference numerals are common with those in FIG. 1, a dried refinery gas stream substantially free of acid gas and $C_5+$ hydrocarbon components is introduced to the LPG separation system through line 1 at a pressure of 12 kg/cm²a. A typical stream composition is:

| Hydrogen | 9.2 mole percent |
|---|---|
| Nitrogen | 4.7 mole percent |
| $CH_4$ | 45.6 mole percent |
| $C_2H_4/C_2H_6$ | 28.4 mole percent |
| $C_3H_6/C_3H_8$ | 9.2 mole percent |
| $C_4H_8/C_4H_{10}$ | 2.6 mole percent |
| $C_5+$ | 0.3 mole percent |

This high pressure gas stream is cooled to −29° C. in exchanger 2 and flashed in drum separator 4. The vapor stream from separator 4 is further cooled to −55° C. in exchanger 7 and flashed in separator 9 from which the vapor portion is further cooled in exchanger 25 to −68° C. and flashed in separator 26 to yield a high pressure gas stream containing substantially all of the starting hydrogen and nitrogen, most of the methane, and about half of the $C_2$ components. This methane-rich stream is expanded across turbine 28, which extracts shaft work for compressor 32, and discharged at a temperature of −92° C. and pressure of 4 kg/cm²a to separator 30 where more of $C_2+$ components are separated as liquid. Refrigeration is recovered from the remaining methane-rich vapor in line 31 through a series of heat exchangers of which only exchanger 25 is shown and the resulting product gas is recompressed in compressor 32 to delivery pressure of 5 kg/cm²a in line 41.

The cold liquid stream 11 from separator 9 is expanded across valve 12 to a pressure of 7 kg/cm²a and provides refrigeration to vapor stream 5 entering exchanger 7. If desired, a portion of this stream may be expanded and taken forward in the process through line 14. Following refrigeration recovery, stream 13 is combined with cold stream 16 which results from expansion of separator 4 liquid and the resulting mixed intermediate pressure stream in line 17 is flashed in separator 18. The resulting liquid stream 20 which contains most of the $C_3+$ components of the starting gas in line 1 provides an enhanced source of refrigeration for the starting gas in exchanger 2 from which it is recovered as stream 23 at a temperature of −4° C. and introduced to de-ethanizer column 36.

The balance of stream 20 not needed in exchanger 2 is sent forward through line 22 and combined with vapor leaving separator 18 prior to introduction to column 36. Since stream 23 is warmer than combined streams 19 and 22, it is evident that stream 17 has been prefractionated into discrete portions prior to introduction to column 36 and thereby reduces separation requirements of the column.

Liquid from separator 26 is expanded across a valve, combined with flow in line 35 and introduced to an upper feed point of column 36. Since this stream is substantially colder than the two lower feeds, it represents an additional prefractionation of the starting gas. De-ethanizer column 36 overhead gas is principally $C_2$ components of the starting gas and is cooled in heat exchanger 38 to −54° C. and flashed in separator 39. Refrigeration is recovered from the resulting vapor stream 40 which is principally $C_2$ hydrocarbons and methane and the resulting warmer stream then combined with product gas discharged from compressor 32.

Since separator 39 is over 1 kg/cm² higher in pressure than separator 30, additional refrigeration is recovered by expanding liquid stream 42 into separator 30 which operates at the discharge pressure of turbine 28. The resulting very cold liquid 33 from separator 30 is increased to column pressure by pump 34 and refrigeration is recovered from the stream in exchanger 25. The resulting relatively warmer stream 35 is then combined with underflow from separator 26 and introduced to the de-ethanizer column.

The function of de-ethanizer column 36 is of course to remove $C_2$ and lighter feed streams from what is to be the desired LPG product removed from the column bottoms. Since the bottoms stream 49 also contains a minor amount of $C_5+$ material, it is further fractionated in debutanizer column 48 which has the principal function of separating $C_3/C_4$ components from a previously separated light gasoline stream introduced through line 50. In customary operation, column 36 bottoms are reboiled through exchanger 44 and column 48 bottoms are reboiled through exchanger 55 while column 48 overhead is cooled and refluxed through exchanger 53. The final separations carried out in column 48 result in recovery of an LPG product stream through line 51 and a light gasoline stream through line 56.

With this two column operation, it is apparent that bottom liquids from column 36 removed through line 49 must again be vaporized in column 48 by reboiler 55. In order to reduce this vaporization requirement, a lighter liquid side stream is removed from an intermediate tray 46 in column 36, vaporized in side reboiler 45 and discharged back into the column below the intermediate tray and a vapor side stream is withdrawn from another intermediate point of column 36 and introduced to column 48 through line 47. Needless to say, reboiler 45 displaces duty that would otherwise be required in reboiler 44.

We claim:

1. A process for separation of a high pressure gaseous stream containing mixed light hydrocarbons which comprises:
    (a) expanding the high pressure gaseous stream to a first intermediate pressure and introducing the resulting expanded stream to a first single equilibrium separation zone;
    (b) recovering a first vapor stream and a separate first liquid stream from the first single equilibrium separation zone;
    (c) elevating the first liquid stream to a second intermediate pressure;
    (d) recovering refrigeration from the first liquid stream at the second intermediate pressure through indirect heat exchange by cooling the high pressure gaseous stream prior to its expansion thereby forming a revaporized stream from the first liquid stream at the second intermediate pressure and introducing the revaporized stream to a multi-equilibrium separation zone;

(e) recovering and cooling an ethane-containing gaseous mixture from the multi-equilibrium separation zone;

(f) introducing the cooled ethane-containing gaseous mixture to a second single equilibrium separation zone;

(g) recovering a second vapor stream and a separate second liquid stream from the second single equilibrium zone; and (h) expanding the second liquid stream into the first single equilibrium separation zone.

2. The process of claim 1 wherein the high pressure gaseous stream is expanded through a turbine.

3. The process of claim 1 wherein the high pressure gaseous stream contains hydrogen, methane, and ethane, the first and second intermediate pressures are between 3 and 35 kg/cm$^2$a, and the high pressure gaseous stream is at a pressure between 5 and 55 kg/cm$^2$a.

4. The process of claim 1 wherein the high pressure gaseous stream contains between 10 and 90 volume percent nitrogen and the first and second vapor streams contain principally nitrogen.

* * * * *